(12) United States Patent
Mustafa

(10) Patent No.: US 9,820,828 B1
(45) Date of Patent: Nov. 21, 2017

(54) REMOVABLE VENEERS FOR TEETH

(71) Applicant: Ibtesam M. Y. Mustafa, Khaldiya (KW)

(72) Inventor: Ibtesam M. Y. Mustafa, Khaldiya (KW)

( * ) Notice: Subject to any disclaimer, the term of this patent is extended or adjusted under 35 U.S.C. 154(b) by 0 days.

(21) Appl. No.: 15/213,322

(22) Filed: Jul. 18, 2016

(51) Int. Cl.
*A61C 5/00* (2017.01)
*A61C 13/267* (2006.01)

(52) U.S. Cl.
CPC ............ *A61C 5/002* (2013.01); *A61C 13/267* (2013.01)

(58) Field of Classification Search
CPC ............................... A61C 5/002; A61C 13/267
See application file for complete search history.

(56) References Cited

U.S. PATENT DOCUMENTS

| | | | | | |
|---|---|---|---|---|---|
| 318,581 | A | * | 5/1885 | Sheffield | A61C 13/26 433/183 |
| 411,538 | A | * | 9/1889 | Stedman | A61C 13/267 433/178 |
| 957,913 | A | * | 5/1910 | Supplee | A61C 13/2255 433/190 |
| 1,519,505 | A | * | 12/1924 | Noyes | A61C 13/267 433/170 |
| 1,746,037 | A | * | 2/1930 | Grove | A61C 13/267 433/170 |
| 1,781,738 | A | * | 11/1930 | Tetreault | A61C 13/267 433/199.1 |
| 2,003,030 | A | * | 5/1935 | Amenta | A61C 13/267 433/178 |
| 2,560,460 | A | * | 7/1951 | MacKey | A61C 13/267 433/170 |
| 3,478,742 | A | * | 11/1969 | Bohlmann | A61C 7/08 128/860 |
| 4,055,895 | A | * | 11/1977 | Huge | A61C 7/08 128/861 |
| 4,514,173 | A | * | 4/1985 | Re | A61C 13/225 433/178 |
| 4,764,115 | A | * | 8/1988 | Willits | A61C 13/24 433/172 |
| 4,799,500 | A | * | 1/1989 | Newbury | A61F 5/01 128/846 |
| 5,022,855 | A | * | 6/1991 | Jeckel | A61C 7/00 433/18 |
| 5,067,896 | A | * | 11/1991 | Korn | A61C 7/08 433/24 |
| 5,096,416 | A | * | 3/1992 | Hulsink | A61C 7/08 433/6 |
| 5,145,364 | A | * | 9/1992 | Martz | A61C 7/00 433/18 |

(Continued)

OTHER PUBLICATIONS

Imako Cosmetic Teeth; http://www.amerimark.com/cgibin/amerimark/index_hom.html.

*Primary Examiner* — Cris L Rodriguez
*Assistant Examiner* — Hao D Mai
(74) *Attorney, Agent, or Firm* — Richard C. Litman

(57) ABSTRACT

The removable veneer for teeth is a cosmetic accessory adapted to overlay the teeth. The accessory includes a veneer designed to simulate perfectly positioned human teeth. A fastener system is employed to removably attach the veneer to the existing natural teeth of a user. Various teeth adornments may be attached to the veneer, if desired, when the wearer wants to assume a more modern look.

3 Claims, 6 Drawing Sheets

(56) References Cited

U.S. PATENT DOCUMENTS

| | | | | |
|---|---|---|---|---|
| 5,203,695 A * | 4/1993 | Bergersen | A61C 7/08 | 128/861 |
| 5,242,304 A * | 9/1993 | Truax | A61C 7/00 | 433/177 |
| 5,415,542 A * | 5/1995 | Kesling | A61C 7/08 | 433/6 |
| 5,431,563 A * | 7/1995 | Huybrechts | A42B 3/12 | 128/862 |
| 5,451,498 A * | 9/1995 | Hazen | A61C 13/24 | 433/167 |
| 5,536,169 A * | 7/1996 | Yousefian | A61C 7/08 | 433/6 |
| 5,607,300 A * | 3/1997 | Tepper | A61C 7/00 | 433/24 |
| 5,810,593 A | 9/1998 | White et al. | | |
| 6,056,546 A * | 5/2000 | Van Handel | A61C 13/225 | 433/168.1 |
| 6,267,596 B1 * | 7/2001 | Kalfas | A61C 13/267 | 433/178 |
| 6,332,774 B1 * | 12/2001 | Chikami | A61C 7/00 | 433/20 |
| 6,790,036 B2 * | 9/2004 | Graham | A61C 7/08 | 128/859 |
| 7,121,825 B2 * | 10/2006 | Chishti | A61C 7/00 | 433/6 |
| 7,955,075 B2 * | 6/2011 | Mailyan | A61C 7/10 | 433/6 |
| 7,963,766 B2 * | 6/2011 | Cronauer | A61C 7/08 | 433/6 |
| 2002/0192617 A1 * | 12/2002 | Phan | A61C 7/00 | 433/6 |
| 2003/0224311 A1 * | 12/2003 | Cronauer | A61C 7/08 | 433/6 |
| 2004/0009449 A1 * | 1/2004 | Mah | A61C 7/10 | 433/7 |
| 2004/0013993 A1 * | 1/2004 | Ito | A61C 7/08 | 433/6 |
| 2005/0003318 A1 * | 1/2005 | Choi | A61C 7/00 | 433/6 |
| 2005/0037312 A1 * | 2/2005 | Uchida | A61C 7/00 | 433/6 |
| 2007/0087300 A1 * | 4/2007 | Willison | A61C 7/12 | 433/6 |
| 2009/0004629 A1 | 1/2009 | Fishman et al. | | |
| 2009/0105523 A1 * | 4/2009 | Kassayan | A61C 7/00 | 600/25 |
| 2010/0104998 A1 * | 4/2010 | Farrell | A61F 5/566 | 433/6 |
| 2010/0129762 A1 * | 5/2010 | Mason | A61C 7/002 | 433/6 |
| 2010/0279245 A1 * | 11/2010 | Navarro | A61C 7/08 | 433/6 |
| 2011/0129786 A1 * | 6/2011 | Chun | A61C 7/08 | 433/19 |
| 2011/0207084 A1 * | 8/2011 | Kaigler, Sr. | A61B 17/663 | 433/174 |
| 2011/0270053 A1 * | 11/2011 | Utley | A61B 5/082 | 600/309 |
| 2011/0311941 A1 * | 12/2011 | Yi | A61C 1/084 | 433/75 |
| 2013/0209952 A1 * | 8/2013 | Kuo | A61C 7/002 | 433/10 |
| 2014/0072926 A1 * | 3/2014 | Valoir | A61C 7/08 | 433/6 |
| 2015/0230886 A1 * | 8/2015 | Badrena Morales | A61C 7/08 | 433/6 |
| 2015/0238283 A1 * | 8/2015 | Tanugula | A61C 7/002 | 433/6 |

* cited by examiner

REMOVABLE VENEERS FOR TEETH

BACKGROUND OF THE INVENTION

1. Field of the Invention

The present invention generally relates to cosmetic dentistry, and particularly to removable veneers for teeth that improve the cosmetic appearance of teeth.

2. Description of the Related Art

First impressions are important in both social and business environments, and such first impressions are often conveyed by a winning smile. Unfortunately, the winning smile may be marred if one's teeth are discolored, crooked or missing. Certain factors (high cost, timing, availability, fear of the dentist, etc.) may prohibit a visit to the dentist for corrective procedures. Nonetheless, one's desire for a pleasing smile is unabated. An unsmiling demeanor or using one's hand to cover the mouth when talking or smiling is very distracting in almost any setting.

Disclosures set out in the related art to allay the above-stated problems have proven to be less than satisfactory. What is needed is a cosmetic accessory that can be easily and instantly attached to one's natural teeth and simulates the look of natural teeth. Thus, removable veneers for teeth solving the aforementioned problems is desired.

SUMMARY OF THE INVENTION

The removable veneers for teeth are cosmetic accessories adapted to overlay the teeth. The accessory includes a veneer designed to simulate perfectly positioned human teeth. A fastener system is employed to removably attach the veneer to the existing natural teeth of a user. Various teeth adornments may be attached to the veneer, if desired, when the wearer wants to assume a more modern look.

Accordingly, the invention presents a cosmetic dental accessory that can be applied without aid from a dentist. The accessory is a veneer adapted to cover the user's unattractive teeth. The veneer simulates natural teeth and may be applied without the use of adhesives and without any risk of pain. The veneer is easy to clean and comfortable to wear. The invention provides for improved elements thereof in an arrangement for the purposes described that are inexpensive, dependable and fully effective in accomplishing their intended purposes.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The removable veneers for teeth are cosmetic accessories adapted to overlay the teeth. The accessory includes a veneer designed to simulate perfectly positioned human teeth. A fastener system is employed to removably attach the veneer to the existing natural teeth of a user. Various teeth adornments may be attached to the veneer, if desired, when the wearer wants to assume a more modern look.

Figure 1A:
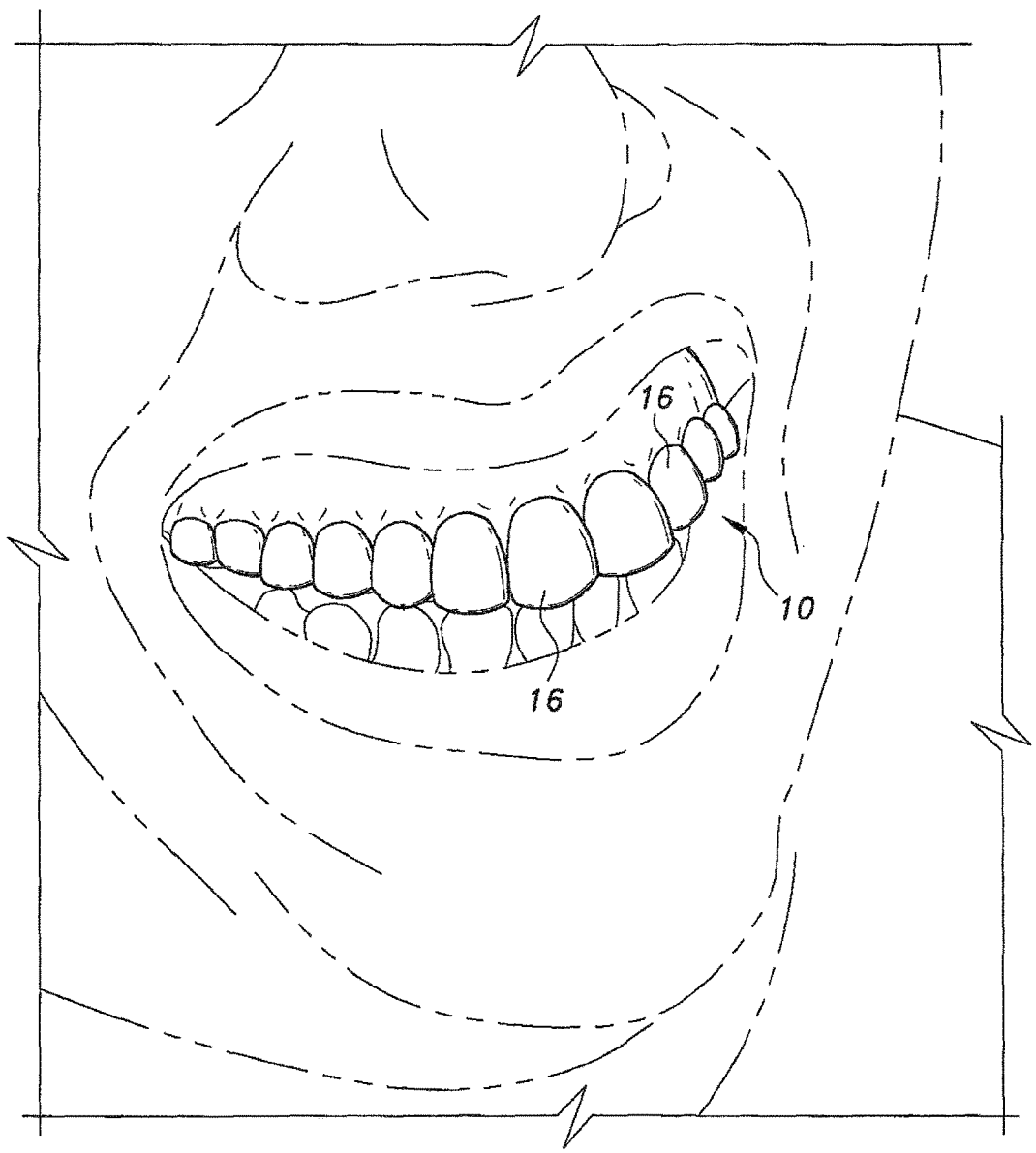
FIG. 1A is an environmental, perspective view of removable veneers for teeth according to the present invention.
Figure 1B:
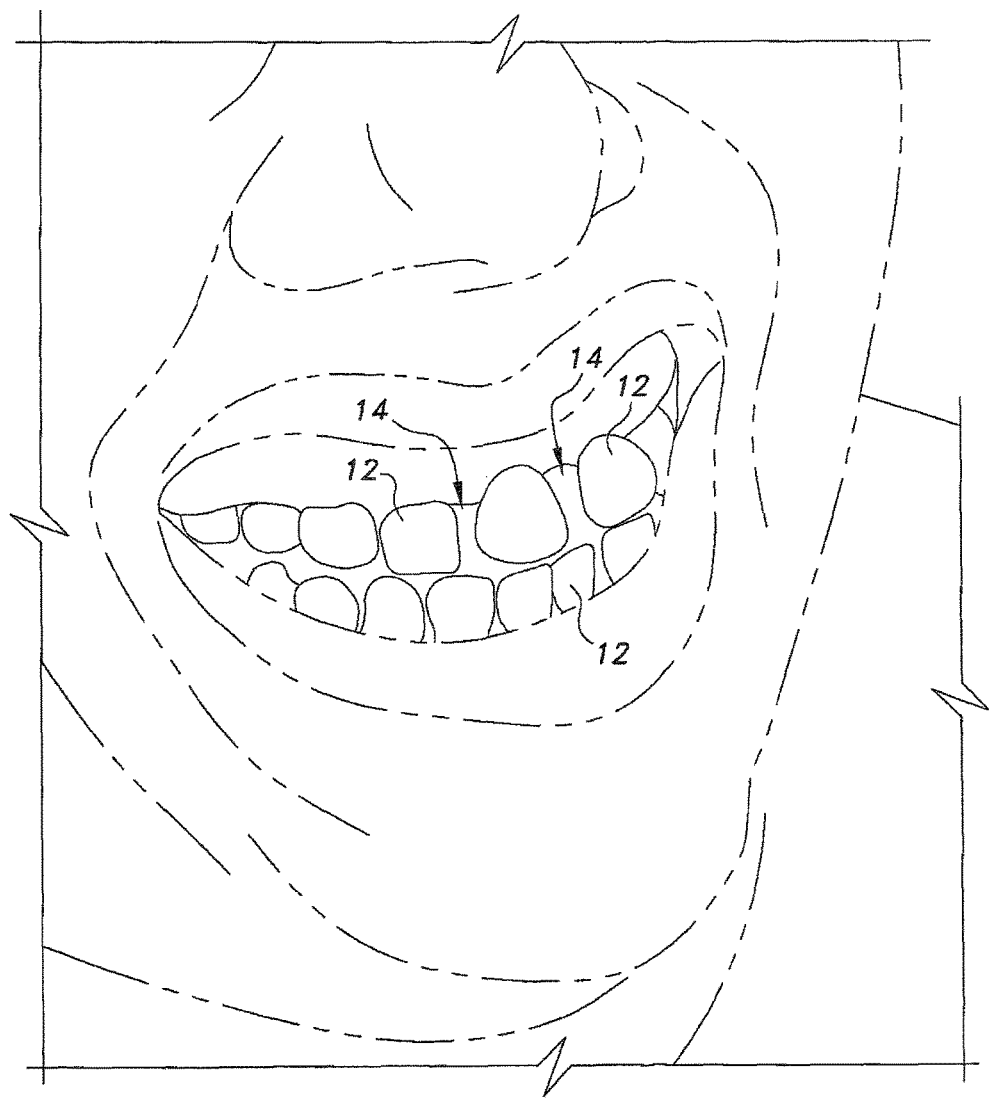
FIG. 1B is a perspective view of a person's mouth before the application of removable veneers for teeth according to the present invention.

FIG. 1B is illustrative of a person's mouth before application of a removable veneer to the teeth 12. Note that the teeth 12 are crooked and formed with relatively wide spaces or gaps 14 therebetween. Upon attaching the veneer, generally indicated at 10 in FIG. 1A, the teeth 16 appear to be perfectly straight, without any wide gaps.

Figure 2:
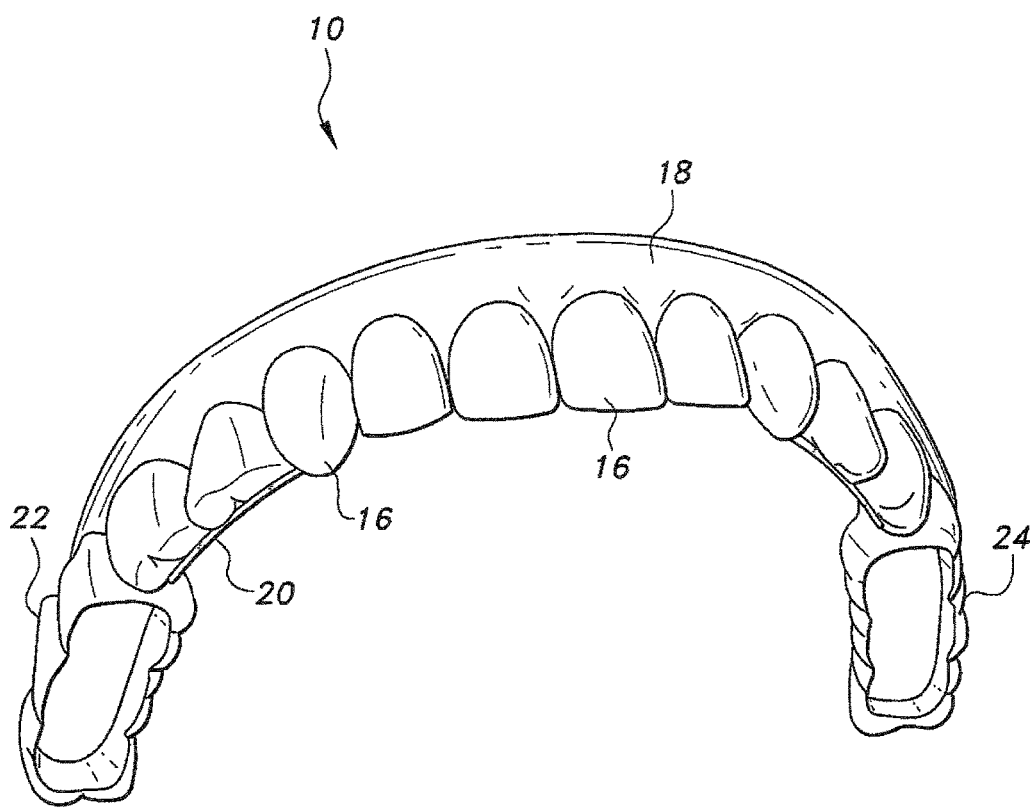
FIG. 2 is a perspective view of a removable veneer for teeth according to an embodiment of the present invention.
Figure 3:
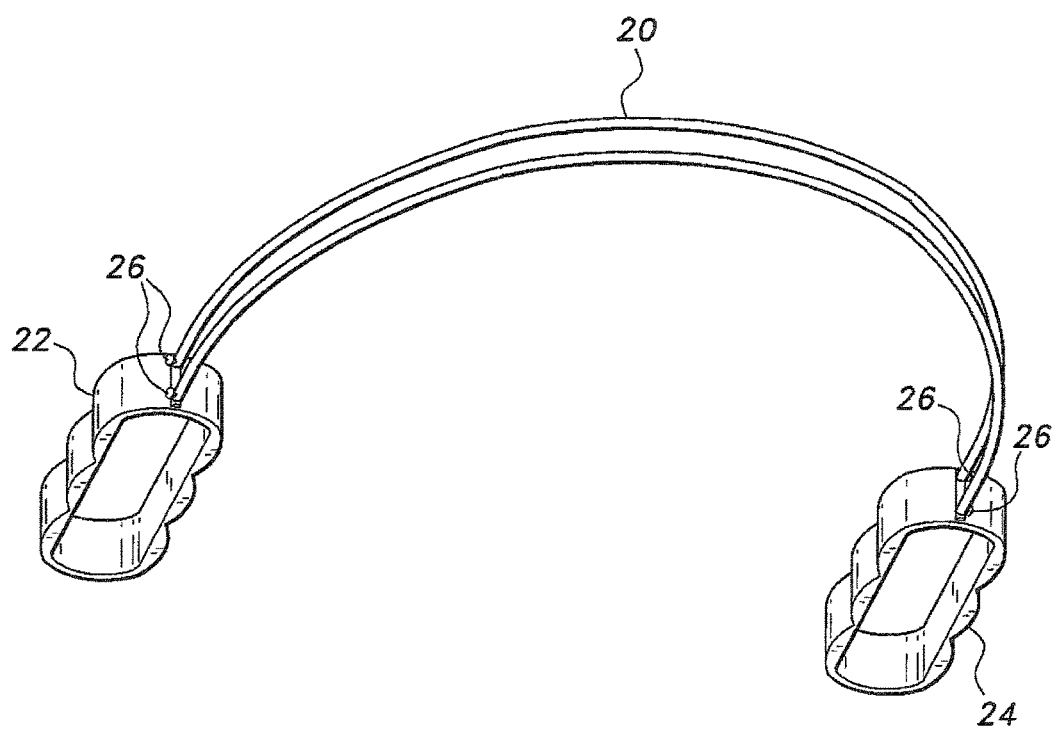
FIG. 3 is a perspective view of a support member for a removable veneer for teeth according to the present invention.

As best seen in FIGS. 2 and 3, the exemplary veneer 10 can include a frame 18 having an anterior surface facing forward and a posterior surface facing rearward. The frame 18 has an array of simulated teeth 16 attached thereto. The simulated teeth 16 can be fabricated from porcelain or other suitable ceramic material and are attached to the anterior surface of the frame 18 by any suitable and efficient method that will not cause a harmful reaction when placed in the mouth of a human, e.g., a biocompatible dental adhesive. A curved or U-shaped brace 20 can be positioned behind the simulated teeth 16. The brace 20 can be attached directly to the frame 18 or the simulated teeth 16. The brace 20 can be formed from metal, plastic, or any other suitable material. The brace 20 can be transparent, plastic, or opaque. Further, the brace 20 can have any suitable width, such as a width of 2 mm or greater.

Figure 5:
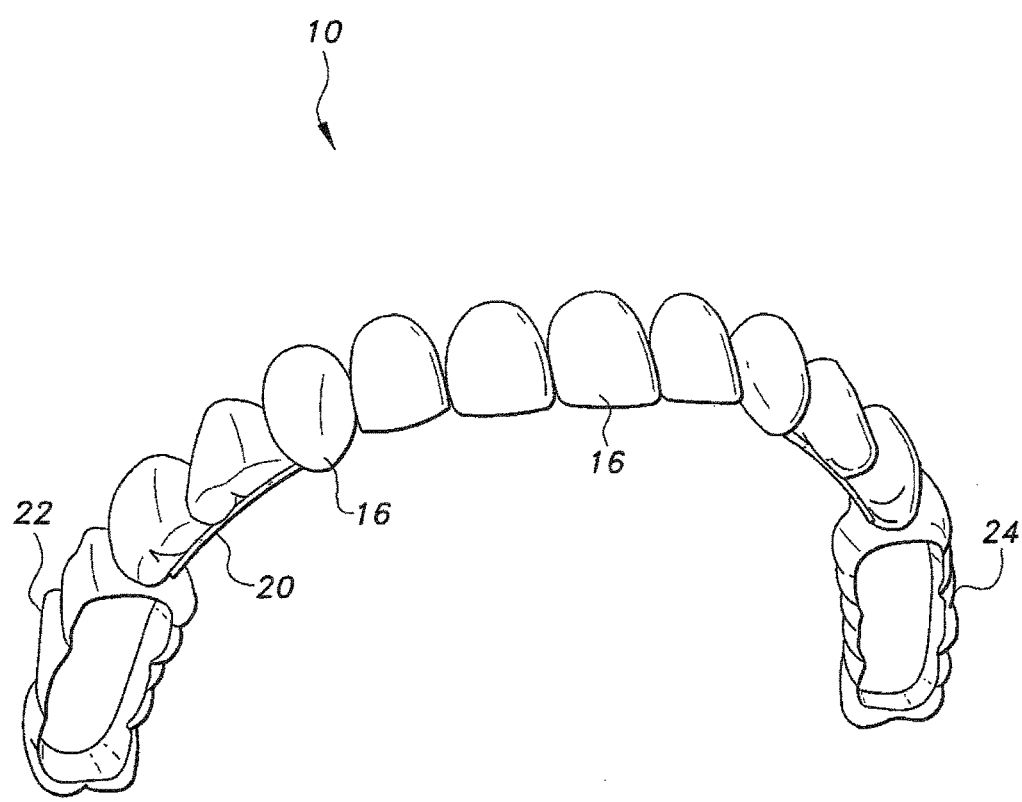
FIG. 5 is a perspective view of a removable veneer for teeth according to an embodiment of the present invention.

The frame 18 is generally U-shaped (conforming to the lower border of the maxilla for the upper teeth, or the mandible for the lower teeth), fabricated from rubber, plastic, metal, or any material that can be designed with a smooth, flesh-like, pinkish finish to resemble human gums. Although the gum-like frame is preferred, it should be noted that the veneer 10 may be designed without the frame 18, as shown in FIG. 5.

The exemplary veneer 10 can include any suitable attachment members for affixing the veneer 10 onto the teeth 12. For example, a first mounting cap 22 and a second mounting cap 24 can be disposed at the ends of the brace 20, as illustrated in FIGS. 2, 3, and 5, or hooks (not shown). The caps 22, 24 can be fitted to the actual size of the user's rear teeth, defining sockets that form a friction fit with the user's rear teeth to retain the veneer 10 in the mouth. Mounting buttons 26, whose function is explained below, are attached to the brace 20 adjacent the inner ends of the mounting caps 22, 24. The attachment members can alternatively include hooks, such as those used for aligning braces. The hooks can be disposed at the ends of the veneer 10 to facilitate directly attaching the veneer 10 on the teeth 12. Utilizing hooks instead of the brace with mounting caps can make the veneer 10 more stable and simpler to use. Although only a veneer component for the upper teeth is illustrated, it is obvious that a similar veneer for the lower teeth can be provided.

By way of operation, the user positions the veneer 10 over the real teeth 12 simply by placing the plurality of attachment members, such as the two caps 22, 24 on the real rear teeth. The mounting buttons 26 are provided to assist the user in the manipulation of the caps 22, 24 during the insertion and removal procedures. The insertion and removal procedures are accomplished without the risk of pain and without the use of any glue or adhesive being applied to the user's real teeth 12.

Figure 4:
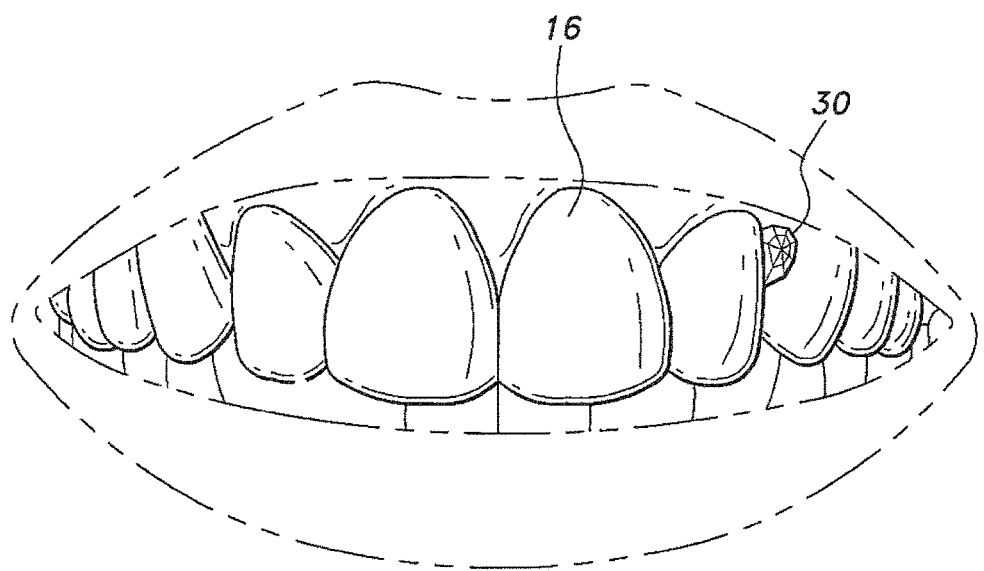
FIG. 4 is an environmental front view of a removable veneer for teeth according to the present invention, shown having an optional ornament attached thereto.

FIG. 4 shows a second embodiment of the removable veneers for teeth wherein the veneer teeth 16 are adapted to support a removable ornament 30 therein, thereby allowing a user to assume a more youthful or modern look. The ornament 30 may be a fine stone or a replica thereof and is positioned between the normal gaps in the teeth.

It is to be understood that the present invention is not limited to the embodiments described above, but encompasses any and all embodiments within the scope of the following claims.

I claim:

1. A removable veneer for teeth adapted to overlie a user's existing natural teeth to improve their cosmetic appearance, consisting of:

a brace having a first end and a second end, an anterior surface facing forward, and a posterior surface facing rearward, wherein the anterior and posterior surfaces are located solely between the first and second ends;

a first and a second attachment members adapted to be attached to rear teeth of the user, the first attachment member being disposed directly at the first end of the brace and the second attachment member being disposed directly at the second end of the brace, wherein each of the first and second attachment members consists solely of a mounting cap mounted on the first and second ends of the brace, respectively, further wherein each of the mounting caps defines solely a socket that is adapted to be mounted to and frictionally fit about the rear teeth of the user; and a plurality of simulated human teeth veneers attached to the brace solely between the first and second ends of the brace, wherein said plurality of simulated human teeth veneers being configured to replicate a row of perfectly positioned human natural teeth consisting of incisors, canines, and premolars, further wherein the plurality of simulated human teeth veneers each has an anterior cosmetic surface and a posterior attachment surface, the posterior attachment surfaces are attached to the anterior surface of the brace, whereby the plurality of simulated human teeth veneers are adapted to overlie existing natural anterior teeth of the user.

2. The removable veneer for teeth according to claim 1, wherein said plurality of simulated human teeth veneers are fabricated from a ceramic material.

3. The removable veneer for teeth according to claim 1, wherein said brace is generally U-shaped.

\* \* \* \* \*